(12) United States Patent
Kjellin et al.

(10) Patent No.: US 12,268,795 B2
(45) Date of Patent: Apr. 8, 2025

(54) ZIRCONIUM AND TITANIUM PHOSPHATE COATINGS FOR IMPLANTS AND OTHER SUBSTRATES

(71) Applicant: Promimic AB, Mölndal (SE)

(72) Inventors: Per Kjellin, Mölndal (SE); Fredrik Currie, Mölndal (SE); Paul Handa, Mölndal (SE); Line Vikingsson, Mölndal (SE)

(73) Assignee: Promimic AB, Mölndal (SE)

( * ) Notice: Subject to any disclaimer, the term of this patent is extended or adjusted under 35 U.S.C. 154(b) by 238 days.

(21) Appl. No.: 16/967,047

(22) PCT Filed: Feb. 8, 2019

(86) PCT No.: PCT/EP2019/053200
§ 371 (c)(1),
(2) Date: Aug. 3, 2020

(87) PCT Pub. No.: WO2019/155021
PCT Pub. Date: Aug. 15, 2019

(65) Prior Publication Data
US 2021/0030921 A1 Feb. 4, 2021

(30) Foreign Application Priority Data
Feb. 9, 2018 (GB) ..................................... 1802184

(51) Int. Cl.
| | | |
|---|---|---|
| A61K 9/16 | (2006.01) | |
| A61L 27/04 | (2006.01) | |
| A61L 27/06 | (2006.01) | |
| A61L 27/32 | (2006.01) | |
| A61L 27/54 | (2006.01) | |
| A61L 27/56 | (2006.01) | |

(52) U.S. Cl.
CPC ............. *A61L 27/32* (2013.01); *A61L 27/047* (2013.01); *A61L 27/06* (2013.01); *A61L 27/54* (2013.01); *A61L 27/56* (2013.01); *A61L 2300/406* (2013.01); *A61L 2400/12* (2013.01); *A61L 2420/06* (2013.01); *A61L 2420/08* (2013.01); *A61L 2430/02* (2013.01); *A61L 2430/12* (2013.01); *A61L 2430/24* (2013.01); *A61L 2430/38* (2013.01)

(58) Field of Classification Search
None
See application file for complete search history.

(56) References Cited

U.S. PATENT DOCUMENTS

| | | | | |
|---|---|---|---|---|
| 5,073,410 A | * | 12/1991 | Paz-Pujalt | ........... C23C 18/1204 427/430.1 |
| 2003/0157349 A1 | | 8/2003 | Kasuga et al. | |
| 2006/0194008 A1 | * | 8/2006 | Schwartz | ................ C23C 14/06 428/34.4 |
| 2009/0093881 A1 | * | 4/2009 | Bandyopadhyay | ....... B22F 1/18 623/23.57 |
| 2013/0306484 A1 | * | 11/2013 | Bandyopadhyay | ... A61L 27/306 205/148 |
| 2019/0350713 A1 | * | 11/2019 | Abele | ..................... A61L 27/20 |

FOREIGN PATENT DOCUMENTS

| | | | |
|---|---|---|---|
| EP | 1911469 | 4/2008 | |
| GB | 1406419 A | 9/1975 | |
| JP | 3076636 | 8/2000 | |
| JP | 2012095735 | 5/2012 | |
| KR | 20120137710 A | 12/2012 | |
| WO | 02087648 A1 | 11/2002 | |
| WO | 03069712 A2 | 8/2003 | |
| WO | 2005123579 A1 | 12/2005 | |
| WO | 2009011489 | 1/2009 | |
| WO | WO-2010049171 A2 * | 5/2010 | ............. A61L 27/02 |
| WO | WO-2011039513 A1 * | 4/2011 | ............. A61L 27/32 |
| WO | 2014048555 A1 | 4/2014 | |

OTHER PUBLICATIONS

Bai et al. "Determination of chromium (III) in natural water samples utilizing capillary micro-extraction on nanometre zirconium phosphate coating coupled to electrothermal atomic absorbance spectrometry" J. Env. Mon., 11(2):326-329 (2009) (Abstract only).
Huang et al. "Advanced anti-corrosion coatings prepared from α-zirconium phosphate/polyurethane nanocomposites" RSC Advances, 7:9908-9913 (2017).
Jimenez Jimenez et al. "Surfactant-Assisted Synthesis of a Mesoporous Form of Zirconium Phosphate with Acidic Properties" Advanced Materials, 10(10):812-815 (1998).
Kraus et al. "Adsorption on Inorganic Materials. I. Cation Exchange Properties of Zirconium Phosphate" Journal of the American Chemical Society, 78(3):694 (1956).
Meirelles et al. "Nano hydroxyapatite structures influence early bone formation" Journal of Biomedical Materials Research, 87A:299-307 (2008).
Nishiyama et al. "Synthesis of Ordered Mesoporous Zirconium Phosphate Films by Spin Coating and Vapor Treatments" Langmuir, 22(23):9469-9472 (2006) (Abstract only).
Wong et al. "Large-scale self-assembled zirconium phosphate smectic layers via a simple spray-coating process" Nature Communications, 5(3589):1-12 (2014).
International Search Report and the Written Opinion of the International Searching Authority corresponding to International Patent Application No. PCT/EP2019/053200 (11 pages) (mailed May 22, 2019).
"Core Equipment and Key Technologies for Modem Digital Healthcare", Chief editor: Wu Qiyao, China Medical Science Press, Mar. 2008, the first version, p. 305.
"Plastic Formula Design and 900 Application Examples", Zong Chengzhong, et al., China Petrochemical Press, Apr. 2002, the first version, p. 51.

(Continued)

*Primary Examiner* — Susan T Tran
(74) *Attorney, Agent, or Firm* — Myers Bigel, P.A.

(57) ABSTRACT

This invention is directed to coated substrates, wherein the coating comprises titanium phosphate and/or zirconium phosphate. In certain embodiments the substrate is an implant for use in vivo. The invention is also directed to methods for forming coatings comprising or consisting of titanium phosphate and/or zirconium phosphate on the surface of a substrate.

27 Claims, 10 Drawing Sheets

(56) References Cited

OTHER PUBLICATIONS

"Polymer Material", Wang Lan et al., China Light Industry Press, Jan. 2009, the first version, p. 376.
English Translation of Office Action issued for Chinese Patent Application No. 201980009971.3 (9 pages) (dated May 11, 2023).
"Experimental Study on Biomodification of Dental Implant Surfaces and Construction of Tissue Engineering Scaffolds", Wu Mingyue, "Chinese National Doctoral Dissertation Full-text Database, Medical and Health Technology Volume", pp. E074-E021 (2011).
"Functional and Intelligent Polymer Materials", Li Qingshan, National Defense Industry Press, Oct. 2006, the first version, p. 237.

\* cited by examiner

ZIRCONIUM AND TITANIUM PHOSPHATE COATINGS FOR IMPLANTS AND OTHER SUBSTRATES

FIELD OF THE INVENTION

The present invention provides coatings which interact favorably with living tissue, such as for example bone tissue and soft tissue. The coatings are highly resistant to mechanical wear and acidic conditions, and can therefore be retained for lengthy periods in vivo. Another object of the invention is to create hydrophilic surfaces, which can be used in various applications. More specifically, coatings of metal phosphates, such as zirconium phosphate and titanium phosphate, are described.

BACKGROUND OF THE INVENTION

Implants are used in various areas of the human body. Dental screws, hip stems and spinal fusion cages are just a few examples of devices which are designed to integrate with bone tissue. Ostomy bag ports, bone anchored hearing aids and dental implant abutments are examples of devices which are designed to integrate with soft tissue.

For successful integration of an implant to human tissue, the choice of implant material is naturally very important. Titanium was discovered in the 1950s to have excellent ability to integrate with bone and also to stimulate the growth of new bone tissue, a phenomenon which is nowadays called osseointegration. Due to these properties and its high mechanical strength, titanium is by far the most common implant material today. Ceramics such as zirconia and alumina toughened zirconia have a slower osseointegration compared to titanium but are used in applications where extreme hardness and strength are demanded, such as hip cups and femoral heads. There are also materials which are classified as bioinert; these are accepted by the human body but do not integrate. Examples of such materials are polymers such as polyamide and polyether ether ketone (PEEK).

Bone consists mainly of a calcium phosphate compound which is chemically and structurally very similar to the mineral hydroxyapatite (HA). To improve the osseointegration, a calcium phosphate coating can be applied on the implant surface. The mechanism of action is not fully understood, but it is generally thought that calcium phosphate triggers bone growth by adsorbing proteins which are involved in the first stages of bone formation. At a later stage, the coating is gradually resorbed and used as a raw material for the formation of new bone. Materials such as tricalcium phosphate (TCP) and HA have a well-documented beneficial effect on bone tissue growth, and these are therefore used clinically in various medical applications, such as bone scaffold materials and implant coatings.

One important parameter of calcium phosphate biomaterials is the resorption speed in vivo. Resorption of endogenous bone is a natural process; old bone is continuously resorbed by osteoclasts and new bone is built by osteoblasts. This resorption releases calcium and phosphorous which can be used as raw materials for new bone. Osteoclasts resorb bone by creating an acidic environment; HA has a very low solubility in neutral pH but is rapidly dissolved below pH 4. An increased solubility in acidic conditions is also observed for other calcium phosphates, such as for example tricalcium phosphate or octacalcium phosphate. For thick (20-60 µm) calcium phosphate based implant coatings the in vivo dissolution may deteriorate the integrity of the coating and cause detachment of large calcium phosphate particles, thus triggering an inflammatory response. For thin (below 1 µm) coatings, the amount of calcium phosphate is very low, and for these coatings the calcium phosphate acts more like a catalyst for bone growth rather than a raw material for bone growth (Meirelles et al. J. Biomed. Mater. Res. A 2 87 299-307). Thin coatings are normally meant to dissolve rapidly in vivo, in the matter of weeks or a few months. After this time the initial steps of osseointegration are finished and the long-term stability of the implant depends on the properties of the substrate. If a thin coating for some reason is dissolved much faster than desired, the efficiency of the coating is greatly reduced. If the substrate itself is a material with poor ability to integrate, this may lead to a very low anchoring strength of the implant since there is a risk that connective tissue will form on the surface instead of bone. PEEK is one example of a bioinert material with poor ability to form bone tissue. It then becomes very important to ensure that a bone stimulating coating is retained over time, at least over the first crucial weeks of osseointegration.

Soft tissue is a broad term for structures in the human body such as skin, tendons, fascia and oral mucosa. While osseointegration is a mature research field and the requirements for a surface which heals into bone are well known, much less is known about soft tissue integration. Generally, a surface which performs well for osseointegration also exhibits good soft tissue integration. Thus, in order to achieve soft tissue integration, the surface should have a high affinity for proteins and a high surface area. Therefore, titanium implants and HA coated implants have been shown to have good soft tissue integration. Porous titanium dioxide ($TiO_2$) and silicon dioxide ($SiO_2$) coatings have also proven to be effective, as described in WO 02/087648.

As mentioned above, calcium phosphate minerals have increased solubility at acidic pH values and resorption of calcium phosphate (CaP) coatings is a natural process in the human body. Another important parameter which affects the in vivo resorption is the adhesion strength of the coating to the substrate. On polymeric materials the bonding strength of a CaP coating to the substrate is considerably weaker than on a highly charged surface such as titanium. Compared to coatings on titanium, coatings on polymers placed in vivo therefore face a higher risk of detachment or delamination of the coating from the polymeric substrate, and a higher dissolution rate.

Zirconium and titanium phosphates (abbreviated ZrP and TiP) are inorganic layered minerals which were initially discovered to possess ion exchange properties (K. A. Kraus et al., JACS, 78 (3) 694, 1956). Nowadays, zirconium phosphate is commonly used in ion exchangers, fuel cells, and as a catalyst material in various applications. Due to its high charge density and ability to adsorb other molecules, ZrP has also been investigated as a vehicle for drug delivery, as an ingredient in polymer composites and in solar energy applications, to name a few examples. ZrP can be synthesised in an aqueous solution, by mixing a water soluble Zr source such as zirconyl chloride ($ZrOCl_2$) with a phosphorus source such as phosphoric acid ($H_3PO_4$). This will precipitate an amorphous or poorly crystalline ZrP. The resulting product can then be transformed to a fully crystalline product by boiling in $H_3PO_4$ or hydrogen fluoride (HF). By varying the synthesis conditions, it is possible to obtain different polymorphs of ZrP, such as for example α-ZrP ($Zr(HPO_4)_2 \cdot H_2O$), and γ-ZrP ($Zr(H_2PO_4)(PO_4) \cdot 2H_2O$). TiP can also be synthesized in aqueous solutions, by mixing a Ti precursor with phosphoric acid. However, Ti precursors such as $TiCl_4$ or titanium alkoxides hydrolyse in water to form TiO$_2$, so the synthesis has to be carried out in such a way that TiO$_2$ formation is prevented.

The initial reports on ZrP synthesis used simple precipitation in aqueous solutions without any structure directing agents to control the particle growth. More recent research has focused on increasing the specific surface area and particle size, often by the use of surfactant systems or other soft templates. Jimenez-Jimenez et al., (Adv. Mater. 1998, (10), 10, 812-815) describe synthesis of ZrP in a surfactant-assisted system with cetyltrimethylammonium (CTMA) bromide as structure directing agent. The result is a semi-crystalline powder with a specific surface area of 250-320 m$^2$/g, but no method of producing a coating of a surface is described.

Yuko et al. (Langmuir 22 (23), 2006, 9469-9472) disclose preparation of ordered mesoporous zirconium phosphate films on a silicon substrate by spin coating using a mixture of zirconium isopropoxide, triethyl phosphate, Pluronic P123 triblock copolymer, nitric acid, ethanol and water. The film thickness was about 275 nm. The film had high proton conductivity.

WO03/069712 discloses proton-conducting ceramic membranes. The membranes comprise a substrate having a coating thereon, wherein the substrate is selected from woven or nonwoven non-electrically conductive fibers. The fibers may be glass fibers, ceramic fibers or a combination thereof. The coating comprises particles of zirconium phosphate having a particle size of less than 5000 nm, preferably 1-100 nm or 10-100 nm. The coating may also comprise agglomerates of zirconium phosphate particles, the agglomerates having a size of 1 μm or more, preferably from 1 to 25 μm.

KR-10-2012-0137710 A discloses an antimicrobial coating composition comprising an antimicrobial compound and a porous material. The porous material may be selected from zeolite, potassium phosphate, zirconium phosphate and silica gel.

WO2014/048555 describes a procedure where a zirconium oxide surface is allowed to react with an acidic sodium phosphate solution to form a monolayer of phosphate ions on the surface which is less than 1.0 nm thick. In this example it was found that the resulting phosphate ion layer adheres very well to the ZrO$_2$ substrate. However, this layer is not a porous ZrP or TiP coating.

US 2003/0157349 disclose an osteoconductive material consisting of a composite coating of a metal hydroxide with surface species such as —ZrOH or —TiOH, on a metal surface. The coating is immersed in a phosphate buffer and heat treated, which results in a phosphate layer on top of the metal hydroxide. This coating consists of phosphate placed on top of a metal hydroxide and does not contain nanosized ZrP or TiP.

A similar approach is described by X. Bai et al (J. Environ. Monit., 2009, 11, 326-329) where a sensor is formed by first producing a coating of ZrO$_2$ on a glass surface, and then applying a phosphoric acid solution to the ZrO$_2$ coating, producing a layer of phosphate on the ZrO$_2$ coating. Note that the authors describe this as a "ZrP coating" but like WO2014/048555 it is a phosphate ion coating on top of a ZrO$_2$ layer. The thickness of this ZrO$_2$/phosphate coating is described to be 0.9 μm.

WO2005/123579 describes the production of nanosized calcium phosphate in the form of a coating or as a powder. This coating method is able to produce very thin (<150 nm) layers of nanosized calcium phosphate. The synthesis of the particles is done by dissolving the precursors in an acidic liquid crystalline phase, and the crystallization is initiated by slowly raising the pH with ammonia. The liquid crystalline phase serves as a structure directing system which restricts the calcium phosphate growth in such a way that nanosized crystals are produced. This method is unsuitable for production of ZrP or TiP, since these materials precipitate at low pH values and addition of the precursors to the liquid crystalline phase would start an immediate reaction between the precursors, which would lead to an uncontrolled crystal growth.

In the literature there are also products described which consist of thin films of ZrP crystals embedded in a polymer matrix, such as for example M. Wong et al. (Nature Comm. DOI: 10.1038/ncomms4589) which describe an epoxy/α-ZrP composite, or T-C Huang et al. (RSC Adv., 2017, 7, 9908-9913), which describe a polyurethane/α-ZrP composite. While these materials can be applied as thin coatings on a surface, the coating will consist of ZrP crystals surrounded by a polymer matrix, and not of pure ZrP.

There is still a need for alternative implants comprising coatings which accelerate tissue integration.

SUMMARY OF THE INVENTION

The present invention provides a substrate comprising a coating on a surface thereof, the coating comprising titanium phosphate, zirconium phosphate or a mixture thereof, wherein the substrate is an implant suitable for use in vivo.

Preferably the coating is a porous coating, preferably with pores with a longest dimension of from 1 to 100 nm. Also preferably the coating consists of titanium phosphate, zirconium phosphate or a mixture thereof.

The coating is preferably amorphous or has a low degree of crystallinity. Also preferably the coating is continuous.

The coating typically has a thickness of from about 1 to about 1000 nm. The ZrP and/or TiP in the coating preferably have a specific surface area of about 5 to about 400 m$^2$/g, as measured with nitrogen adsorption.

In another embodiment, the present invention provides a substrate comprising a porous coating on a surface thereof, the coating comprising titanium phosphate, zirconium phosphate or a mixture thereof, wherein the coating has a thickness of 1 to 99 nm. Preferably the coating consists of titanium phosphate, zirconium phosphate or a mixture thereof. The coating is a porous coating, preferably with pores with a longest dimension of from 1 to 100 nm.

The coating typically has a thickness of from about 1 to about 1000 nm. The ZrP and/or TiP in the coating preferably have a specific surface area of about 5 to about 400 m$^2$/g, as measured with nitrogen adsorption.

Preferably, the coating is amorphous or has a low degree of crystallinity. Also preferably the coating is continuous.

The invention also provides a first method for forming a coating comprising or consisting of zirconium phosphate on a surface of a substrate, the method comprising:
a) mixing a first water-in-oil emulsion comprising a zirconium precursor with a second water-in-oil emulsion comprising a phosphate precursor, and allowing the zirconium precursor and the phosphate precursor to react together to form a dispersion of nanosized zirconium phosphate particles;
b) applying said dispersion to the surface of the substrate;
c) optionally creating an even layer of the dispersion on the surface of the substrate; and
d) removing any other components of the dispersion in order to form the coating of zirconium phosphate on the surface of the substrate.

In an alternative to the above method, step a) above can be replaced by step a1):

a1) adding a phosphate precursor to a water-in-oil emulsion comprising a zirconium precursor, or adding a zirconium precursor to a water-in-oil emulsion comprising a phosphate precursor, and allowing the zirconium precursor and the phosphate precursor to react together to form a dispersion of nanosized zirconium phosphate particles.

The invention further provides a second method for the formation of a coating comprising or consisting of titanium phosphate on a surface of a substrate, the method comprising:

e) adding a titanium precursor to a water-in-oil emulsion comprising a phosphate precursor, and allowing the titanium precursor and the phosphate precursor to react together to form a dispersion of nanosized titanium phosphate particles;

f) applying said dispersion to the surface of the substrate;

g) optionally creating an even layer of the dispersion on the surface of the substrate; and h) removing any other components of the dispersion in order to form the coating of titanium phosphate on the surface of the substrate.

The invention further provides a third method for the formation of a coating comprising or consisting of titanium phosphate and/or zirconium phosphate on a surface of a substrate, the method comprising:

a) mixing a solution comprising a zirconium precursor and/or a titanium precursor in an organic (non-aqueous) solvent with a water-in-oil emulsion comprising a phosphate precursor, and allowing the zirconium precursor and/or titanium precursor and the phosphate precursor to react together to form a dispersion of nanosized zirconium phosphate and/or titanium phosphate particles;

b) applying said dispersion to the surface of the substrate;

c) optionally creating an even layer of the dispersion on the substrate; and d) removing any other components of the dispersion in order to form the coating of zirconium phosphate and/or titanium phosphate on the substrate.

The invention further provides method for increasing the hydrophilicity of a surface of a substrate, the method comprising forming a coating on the surface of the substrate using any of the methods of the invention described above. Preferably, the substrate is a polymeric substrate, more preferably PEEK.

The invention also provides coated substrates obtainable by any of the methods of the invention.

The substrates may be implants such as dental screws, hip stems, spinal fusion cages, ostomy bag ports, bone anchored hearing aids, dental implant abutments and external fixation devices. The substrates may also be structures where a hydrophilic surface is desirable, such as components of sensors or medical devices.

DETAILED DESCRIPTION OF THE INVENTION

Figure 1A:
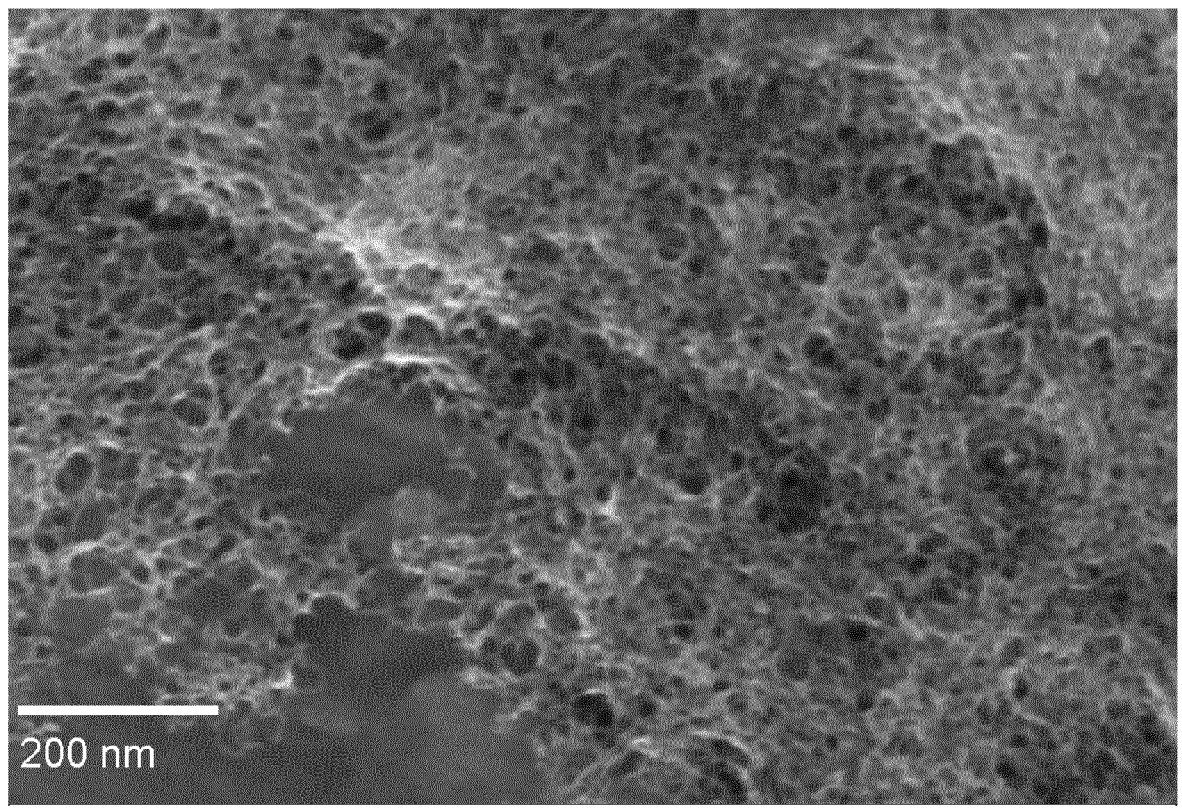
FIG. 1a. SEM image of ZrP coating of the invention on a titanium disc, using a Pluronic L64/p-xylene/water system. Scale bar=200 nm.

Unless otherwise stated, the following discussion applies to any type of substrate and to all embodiments of the invention.

The coatings of the present invention are formed from titanium phosphate (TiP) and/or zirconium phosphate (ZrP). Preferably they are formed directly on the surface of the substrate, with no intervening layers or coatings. An acidic phosphate-based material such as ZrP or TiP will interact strongly with surfaces which are able to form bonds with phosphate groups. Therefore, the coatings have a high adhesion strength to metals such as titanium and zirconium, but also to ceramics such as $ZrO_2$ and $Al_2O_3$, and polymers such as PEEK. Like HA, ZrP adsorbs strongly to proteins and amino acids, but one significant difference between HA and ZrP is the stability at different pH. While HA is stable under basic conditions and starts to dissolve at low pH values, the behaviour of ZrP is the opposite, as it is stable at low pH values but starts to dissolve under basic conditions. This makes ZrP highly resistant to the acidic environment created in the natural dissolution processes in the human body. TiP has similar properties as ZrP regarding protein adsorption and stability at acidic conditions, but has a higher solubility at alkaline pH values. Coatings of ZrP and TiP will therefore be long lasting in vivo, for example essentially permanent.

An implant coating of ZrP or TiP will be resistant to acidic conditions, and will also have a high tendency for protein adsorption. Further, a coating with features in the nanometer range will increase the surface energy and specific surface area of the underlying substrate, which improves the adhesion of proteins. Such a coating will also increase the hydrophilicity of the substrate in question, whether it is a polymer such as PEEK, or a metal such as titanium. A hydrophilic surface is desirable for osseointegration and soft tissue integration, but a hydrophilic surface is also attractive in other applications, for example to help prevent bubble formation in sensors and to increase wetting for catheters. Since the coating can be made very thin and continuous, it will follow the underlying structure of an implant, thereby making it possible to retain the topography of the implant surface. Since many commercial implants are processed to have a surface roughness in the micrometer range (usually 0.5-2 μm in arithmetical mean height of the surface ($S_a$)), a coating on top of these surfaces has to be thin if the micron-sized roughness is to be preserved.

Materials such as ZrP or TiP are more brittle than a polymer or a metal, and this difference in mechanical properties can lead to problems if the coating is too thick. For example, if a coated polymeric material is subjected to bending forces, the dimensional deformation in the coating and in the polymeric substrate will be completely different. Since for a given geometry the flexibility of any material increases when its thickness decreases, a thin coating will be more resilient to bending than a thick coating. It is therefore advantageous to have a thinner ZrP or TiP coating when the substrate is a polymeric or metallic substrate.

Substrate

The coating can be applied to any suitable substrate, including, but not limited to, substrates made from metals such as titanium and its alloys, zirconium and its alloys, stainless steel, tantalum, NiTi alloys and cobalt-chrome alloys; ceramics such as alumina, zirconia, alumina toughened zirconia, and $Si_3N_4$; graphitic material such as graphene and pyrocarbon; silicon; and polymers such as polypropylene, polyethylene, polysulfone (PSU), polyether ketone ketone (PEKK), poly(styrene), poly(carbonate), poly(ethylene terephthalate) and PEEK. Preferred substrates include titanium and its alloys, zirconium and its alloys, stainless steel, tantalum, NiTi alloys, cobalt-chrome alloys, alumina, zirconia, alumina toughened zirconia, pyrocarbon, polysulfone (PSU), polyether ketone ketone (PEKK), poly(styrene), poly(carbonate) and PEEK. More preferred substrates include titanium and its alloys, stainless steel, zirconia, alumina toughened zirconia, pyrocarbon, and PEEK, most preferably PEEK.

Preferred substrates are in the form of implants for use in vivo. For implants, the substrate is preferably biocompatible. Suitable implants include dental screws, hip stems, spinal fusion cages, ostomy bag ports, bone anchored hearing aids, dental implant abutments and external fixation devices. Preferred are implants with roughened surfaces for the purpose of accelerating integration once implanted into a human or animal body. Preferred substrates for implants include titanium and its alloys, stainless steel, cobalt-chrome alloys, zirconia, alumina toughened zirconia, pyrocarbon, and PEEK, most preferably PEEK.

The ZrP and TiP coatings of the present invention are hydrophilic. The substrate can therefore also be any device or component thereof for which it is beneficial that the surface of the device or component is hydrophilic. Preferred substrates to be rendered hydrophilic include polymeric substrates, particularly PEEK substrates. For example, bubble formation may sometimes distort measurements using sensors. Bubbles tend to adhere to hydrophobic surfaces and therefore rendering the surface of a sensor hydrophilic by coating it with ZrP and/or TiP according to the present invention could help prevent bubble formation. Other substrates for which a hydrophilic surface may be preferred include catheters, tubing, nozzles and cables, for example cables made from polymeric material such as PEEK. Further preferred substrates are therefore sensors or sensor components, catheters and tubing.

Coated substrates of the invention may also be useful in membrane separation, optical devices, electronic devices including membrane electrode assembly, and fuel cells.

Coating

The coating may be present over the whole surface of a substrate or only part of the surface. For an implant, at least 25% (by area) of the body-facing surface of the implant is preferably coated, more preferably at least 40%, at least 50%, or at least 70%.

A thin coating is desirable in order in preserve the underlying surface morphology. Thick coatings may crack or show a tendency to delaminate for the substrate. Preferably, when the substrate is an implant, the thickness of the coating is therefore no more than 1000 nm, for example from about 1 to about 1000 nm or from about 5 to about 1000 nm. The lower limit for the thickness is preferably at least about 1 nm, more preferably at least about 3 nm and even more preferably at least about 5 nm, for example at least about 10 nm. The upper limit for the thickness is preferably no more than about 500 nm, more preferably no more than about 300 nm, and even more preferably no more than about 250 nm, for example no more than about 200 nm. More preferably, the thickness of the coating is in the range from about 5 to about 150 nm, or from about 5 to about 100 nm. Most preferably, the thickness of the coating is from about 10 to about 40 nm. Ranges obtained by combining any of the above lower limits with any of the above upper limits are also included in the present invention.

For other types of substrate, the thickness of the coating is below 100 nm, preferably about 1 to about 99 nm. The lower limit for the thickness is preferably at least about 1 nm, more preferably at least about 3 nm and even more preferably at least about 5 nm, for example at least about 10 nm. The upper limit for the thickness is preferably no more than about 95 nm, more preferably no more than about 80 nm, and even more preferably no more than about 40 nm. More preferably, the thickness of the coating is in the range from about 5 to about 95 nm, or from about 5 to about 80 nm. Most preferably, the thickness of the coating is from about 10 to about 40 nm. Ranges obtained by combining any of the above lower limits with any of the above upper limits are also included in the present invention.

Preferably, the specific surface area of the ZrP and/or TiP in the coating, as measured via nitrogen adsorption and using the Brunauer-Emmett-Teller (BET) model, is from about 5 to about 400 $m^2/g$. More preferably, the specific surface area is in the range of about 50-350 $m^2/g$. Even more preferably, the specific surface area is in the range of about 100-250 $m^2/g$. It is not possible to measure the specific surface area of the ZrP and/or TiP in the coating directly. Rather it may be measured by calcining (burning) a portion of the coating dispersion and analyzing the powder obtained.

The coatings of the invention are preferably porous. By porous is meant that the coating is able to absorb gases or liquids. Preferably the coating has pores with a longest dimension of from about 1 to about 100 nm. As used herein, coatings formed of particles of ZrP or TiP are also considered to be porous if there are spaces between adjacent particles in the coating which allow for absorption of gases or liquids. Pore size may be measured using SEM and image analysis. The specific surface area also serves as an indirect measurement of the porosity of the coatings. A higher specific surface area will generally correspond to a more porous coating.

As mentioned above, many implants have roughened surfaces with the purpose of accelerating integration in vivo. The present invention makes it possible to produce very thin coatings which preserve the underlying surface morphology of the substrate, thus making it possible to coat micrometer-range features without significantly changing the roughness.

Measurement of the coating thickness can be done in several ways. For an extremely thin coating, with a thickness of 1-10 nm, a rough estimate of the thickness can be made using X-ray photoelectron spectroscopy (XPS). Since XPS measures the atomic content from the uppermost 10 nm of a substrate, an XPS measurement which returns signals from the underlying substrate shows that the thickness of the coating is in the 1-10 nm range, provided that the coating is homogenous and evenly distributed. For a thicker coating, for example >10 nm to <100 nm, the thickness can for example be measured by dissolving the coating in a strongly alkaline medium and measuring the atomic content of the extracted media with Inductively Coupled Plasma Atomic Emission Spectroscopy (ICP-AES). Another method to measure a coating in this thickness range is by doing a milling and lift-out procedure with subsequent Transmission Electron Microscopy (TEM) analysis. Thicker coatings (>100 nm) can be measured by examining cross sections of the coated substrate using Scanning Electron Microscopy (SEM).

Preferably, the coatings are formed from amorphous or low crystallinity ZrP and/or TiP. Amorphous or low crystallinity ZrP or TiP can be converted into highly crystalline ZrP or TiP by suitable treatment, but this is optional. Methods for the conversion of amorphous or low crystallinity ZrP or TiP into highly crystalline material are known in the art. However, conversion to highly crystalline ZrP or TiP generally requires treatment with boiling phosphoric or hydrofluoric acid, or heat treatment. It is not therefore suitable unless the substrate is resistant to the treatment conditions.

Methods

The invention also provides methods for forming ZrP and/or TiP coatings on substrates, and methods for improving or increasing the hydrophilicity of substrates.

The invention provides a first method for forming a coating comprising or consisting of zirconium phosphate on a surface of a substrate, the method comprising:
- a) mixing a first water-in-oil emulsion comprising a zirconium precursor and optionally a surfactant with a second water-in-oil emulsion comprising a phosphate precursor and optionally a surfactant, and allowing the zirconium precursor and the phosphate precursor to react together to form a dispersion of nanosized zirconium phosphate particles;
- b) applying said dispersion to the surface of the substrate, preferably by dropwise addition, spraying or by dipping the substrate into the dispersion;
- c) optionally forming an even layer of the dispersion on the surface of the substrate, preferably by rotation of the substrate, capillary extraction, by the use of gravimetric force or by applying a stream of compressed gas onto the substrate; and
- d) removing any other components of the dispersion, preferably by heat treatment, plasma treatment, liquid extraction or by a combination of these, in order to form the coating of zirconium phosphate on the surface of the substrate.

In an alternative to the above method, step a) above can be replaced by step a1):
- a1) adding a phosphate precursor to a water-in-oil emulsion comprising a zirconium precursor and optionally a surfactant, or adding a zirconium precursor to a water-in-oil emulsion comprising a phosphate precursor and optionally a surfactant, and allowing the zirconium precursor and the phosphate precursor to react together to form a dispersion of nanosized zirconium phosphate particles.

The invention further provides a second method for the formation of a coating comprising or consisting of titanium phosphate on a surface of a substrate, the method comprising:
- e) adding a titanium precursor to a water-in-oil emulsion comprising a phosphate precursor and optionally a surfactant, and allowing the titanium precursor and the phosphate precursor to react together to form a dispersion of nanosized titanium phosphate particles;
- f) applying said dispersion to the surface of the substrate, preferably by dropwise addition, spraying or by dipping the substrate into the dispersion;
- g) optionally forming an even layer of the dispersion on the surface of the substrate, preferably by rotation of the substrate, capillary extraction, by the use of gravimetric force or by applying a stream of compressed gas onto the substrate; and
- h) removing any other components of the dispersion, preferably by heat treatment, plasma treatment, liquid extraction or by a combination of these, in order to form the coating of titanium phosphate on the surface of the substrate.

The invention further provides a third method for the formation of a coating comprising or consisting of titanium phosphate and/or zirconium phosphate on a surface of a substrate, the method comprising:
- a) mixing a solution comprising a zirconium precursor and/or a titanium precursor and optionally a surfactant in an organic (non-aqueous) solvent with a water-in-oil emulsion comprising a phosphate precursor and optionally a surfactant, and allowing the zirconium precursor and/or titanium precursor and the phosphate precursor to react together to form a dispersion of nanosized zirconium phosphate and/or titanium phosphate particles;
- b) applying said dispersion onto a solid surface, preferably by dropwise addition, spraying or by dipping the substrate into the dispersion;
- c) optionally forming an even layer of the dispersion on the substrate, preferably by rotating, capillary extraction, by the use of gravimetric force or by applying a stream of compressed gas onto the substrate; and
- d) removing any other components of the dispersion, preferably by heat treatment, plasma treatment, liquid extraction or by a combination of these, in order to form the coating of zirconium phosphate and/or titanium phosphate on the substrate.

The invention further provides method for increasing the hydrophilicity of a surface of a substrate, the method comprising forming a coating on the surface of the substrate using any of the methods of the invention described above.

In the methods of the invention, nanosized refers to particles with a longest dimension of from 1 to 100 nm.

Preferably, each of the starting emulsions and solutions for use in the methods of the invention also comprise one or more surfactants.

The titanium precursor may be any suitable titanium salt or compound which can be dissolved in a suitable organic solvent, including titanium tetrachloride ($TiCl_4$), titanium ethoxide, titanium isopropoxide and titanium diisopropoxide bis(acetylacetonate). Many titanium compounds including $TiCl_4$ and titanium isopropoxide will hydrolyse to form titanium dioxide when in contact with water. For the synthesis of titanium phosphate coatings, it is therefore important to avoid premature contact of the titanium precursor with water. Preferred titanium precursors are therefore compounds which are soluble in organic solvents. Titanium salts or compounds which are insoluble in water such as titanium dioxide, titanium sulfate, titanium carbide, or titanium phosphate are not suitable for use as precursors.

The zirconium precursor may be any suitable zirconium salt or compound, including zirconium tetrachloride ($ZrCl_4$), zirconyl oxychloride, zirconyl nitrate, zirconium ethoxide, zirconium isopropoxide and zirconium diisopropoxide bis(acetylacetonate). For use in the first method, the zirconium precursor should be soluble in water, such that it is present in the aqueous phase of the water-in-oil emulsion. Suitable water soluble precursors include zirconium tetrachloride, zirconyl oxychloride and zirconyl nitrate. For use in the third method, the zirconium precursor should be soluble in an organic solvent. Suitable organic-soluble precursors include zirconium ethoxide, zirconium isopropoxide and zirconium diisopropoxide bis(acetylacetonate).

The phosphorous precursor may be phosphoric acid ($H_3PO_4$), $Na_3PO_4$, $Na_2HPO_4$, $NaH_2PO_4$, $K_3PO_4$, $K_2HPO_4$, $KH_2PO_4$, phosphorous acid ($H_3PO_3$), hypophosphorous acid ($H_3PO_2$), or phosphorous acid esters such as triethyl phosphite. Preferably, the phosphorous precursor is soluble in water, such that it is present in the aqueous phase of the water-in-oil emulsion.

The metal precursor and the phosphate precursor may be used in any suitable molar ratio, for example to provide a molar ratio of Zr to phosphate of from about 1:1 to about 1:3 or a molar ratio of titanium to phosphate of about 1:2.

The water-in-oil emulsions used in the methods of the invention are preferably microemulsions. The emulsions typically contain surfactants, but potentially any surfactant-stabilized system with nanosized aqueous domains can be used. Microemulsions generally comprise a dispersed phase present as droplets or domains from about 1 to 100 nm in diameter, for example about 10-50 nm in diameter, dispersed within a continuous phase. In a water-in-oil microemulsion, water forms the dispersed phase whilst an organic solvent (oil) which is immiscible or substantially immiscible with water forms the continuous phase. A surfactant is normally present at the interfaces between the dispersed phase and the continuous phase in order to help stabilize the emulsion (K. Holmberg et al. Surfactants and Polymers in aqueous solutions, Wiley, ISBN 0-471-49883-1). One beneficial property of a microemulsion is the ability to wet and spread onto almost any surface; whether it is a polar and hydrophilic surface such as titanium, or a non-polar and hydrophobic surface such as PEEK.

Without being bound by theory, it is believed that the, preferably surfactant-lined, dispersed water domains in the starting water-in-oil emulsion(s) function as nanosized (e.g. with a diameter in the range of about 1 to about 100 nm) reaction vessels which prevent growing particles of ZrP or TiP from colliding and growing to larger aggregates. The result is a dispersion where the water domains contain dispersed nanosized ZrP or TiP particles.

Emulsions for use in the methods of the invention can be formed using various surfactant/solvent/water combinations. Surfactants suitable for use in the methods herein include but are not limited to: nonionic surfactants such as poly(propylene oxide) (PPO)-poly(ethylene oxide) (PEO) surfactants, for example PEO-PPO-PEO and PPO-PEO-PPO surfactants, alcohol ethoxylates (C-EO), polysorbates, straight chain alcohols, fatty acid amides, alkylphenol ethoxylates and polyglycerol alkyl ethers, anionic surfactants such as alkyl phosphates, alkyl sulfonates and alkyl sulfates and cationic surfactants such as quaternary ammonium salts. Preferred surfactants include the poly(ethylene oxide)-poly(propylene oxide)-poly(ethylene oxide) (PEO-PPO-PEO) block copolymers Pluronic L64 and Pluronic P84 and alkylphenol ethoxylates. Suitable alkylphenol ethoxylates include those available from The Dow Chemical Company under the Triton trademark, for example Triton X-100 which has CAS registry number: 9002-93-1 and is characterised by the following formula:

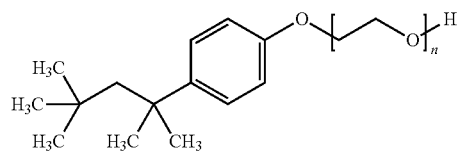

wherein n is 9-10.

Organic solvents suitable for creating the starting emulsions or solutions include any solvent which is immiscible or substantially immiscible with water, such as aliphatic, aromatic and cyclic hydrocarbons, alcohols, esters, ethers, ketones, and mixtures thereof. Preferred organic solvents include p-xylene, cyclohexane and hexadecane, and combinations thereof.

If two different emulsions or an emulsion and an organic solution are used in the methods disclosed herein, it is preferred that the same organic solvent is used in both. Similarly, it is preferred that the same surfactant is used in both.

In the mixing steps of the methods of the invention, the mixing should be continued for a sufficient period of time to allow the metal precursor and the phosphate precursor to react together to form TiP or ZrP. Typically, the mixing should continue for about 5 to 24 hours, preferably about 6 hours, to ensure the reaction is complete. As ZrP and TiP are insoluble in water and the organic solvents used, they precipitate out, resulting in a colloidal dispersion of ZrP and/or TiP. A colloidal dispersion as used herein refers to particles of about 1 to about 1000 nm in size, dispersed in liquid.

Application of the dispersion to the surface of a substrate may be carried out using any technique known in the art, including spraying, dip-coating or by dropwise addition. A device such as a spin coater can be used to control the thickness of the coating liquid layer by removing excess coating dispersion and to spread out the liquid to create an even layer over all desired surfaces of the substrate.

Once the coating dispersion has been applied to a substrate, components of the dispersion other than the TiP or ZrP, including the water, the organic solvent(s) and any surfactant(s), must be removed to leave only a layer of zirconium or titanium phosphate. This results in the nanosized particles of ZrP and/or TiP agglomerating or fusing together to form a continuous, porous coating. Drying can be used to remove water and any organic solvents, but other methods may be required to remove any surfactant(s) present. A convenient way to remove all other components is to perform a heat treatment, at a temperature high enough to combust the surfactant(s) and evaporate water and organic solvent(s). Heat treatment may also increase the adhesion between the phosphate compound and the substrate, and has the additional benefit of providing a sterile coated substrate, which is attractive to be able to implement the coating process in an industrial environment. Since the layer of coating dispersion is so thin, the heat treatment can be done for short periods of time, no more than about 5-10 minutes. This brief heat treatment does not affect the mechanical properties of the substrate material. Suitable temperatures for the heat treatment are about 300-550° C. for metals such as titanium, and about 300-350° C. for polymers such as PEEK.

Another method for removing the organic and aqueous components of the coating dispersion is to perform an extraction using a suitable solvent, such as isopropanol or p-xylene, to remove the surfactants and solvents. This method is especially suited for materials which cannot withstand high temperature treatments, for example low melting point polymers.

Yet another way to remove the organic and aqueous components of the coating dispersion is to use a plasma cleaner. By treating the implant surface with ionized gas (plasma) in a vacuum chamber, any organic components of the dispersion such as the surfactant(s) may be fully oxidized and removed whist water and organic solvent will be evaporated.

One advantage of the methods of the invention is that they can be used to form coatings, preferably continuous coatings, over all exposed surfaces of a substrate, including substrates with complex geometries. This is particularly advantageous with implants made from polymers, as these often have complex geometries and may be difficult to coat over all surfaces using conventional techniques. Since the methods of the invention are wet chemical techniques, in contrast to line of sight techniques such as chemical vapour deposition, physical vapour deposition or plasma spray, they are highly suitable for use in coating complex structures which have been 3D-printed (additive manufacturing) or to coat structures such as metal foams.

As previously mentioned, many implants have roughened surfaces with the purpose of accelerating the integration. The methods of the invention make it possible to produce very thin coatings which makes it possible to coat micrometer-range features without significantly changing the roughness. The thickness of the coating can be varied by, for example, changing the concentrations of the precursors in the starting emulsions or solutions, by changing the rotational speed during a spin coating procedure and/or by applying compressed air during a spin coating procedure. Another method to control the thickness on porous structures, such as 3D-printed structures or metal foams, is to remove an amount of the coating microemulsion from the structure by capillary extraction before the drying step. In this method, the coated substrate is placed onto a porous material with the capability of extracting the coating liquid from the coated substrate. Depending on the material, pore size and thickness of the porous material, the amount of extracted coating liquid can be varied, which in turn affects the thickness of the coating layer after it is dried.

The TiP and/or ZrP coatings render the surface of the substrate to which they are applied hydrophilic, for polymers, or super hydrophilic (water contact angle <10°) for metals. The invention therefore further provides a method for increasing the hydrophilicity of a surface of a substrate, the method comprising forming a coating on the surface of the substrate using any of the methods of the invention described above.

Whilst porous coatings are preferred for implants, non-porous coatings may also be used. Non-porous coatings may be formed on substrates using chemical vapour deposition, physical vapour deposition or plasma spray techniques. However, these techniques are line of sight techniques which may not be suitable to coat complex structures such as roughened surfaces, 3D-printed structures or metal foams.

Once formed, the TiP and ZrP coatings may be functionalized, for example by addition of a further coating layer and/or an active compound. Active compounds may be adsorbed by the coating or may attach to it. Suitable active compounds include substances which stimulate bone growth or which prevent bacterial growth. Substances which are able to stimulate bone tissue growth including, but are not limited to: bone morphogenetic proteins (BMP), bisphosphonates, calcium phosphates, calcium ions and magnesium ions. It is also possible to functionalize the coating with the adhesion of substances which prevent bacterial growth, including but not limited to: antibiotics such as gentamicin or chlorohexidine, endogenous substances such as defensins, or inorganic antibiotic agents such as silver or zinc.

Functionalisation may be carried out by soaking the coated substrate in a solution or dispersion of the desired active compound or a mixture of active compounds.

Further coating layers may be deposited on top of the TiP or ZrP coating using known techniques for coating substrates. For example, a hydroxyapatite or other calcium phosphate layer may be deposited using the method of WO2005/123579. Preferred additional coating layers comprise amorphous calcium phosphate, monocalcium phosphate, dicalcium phosphate, tricalcium phosphate, tetracalcium phosphate, hydroxyapatite, octacalcium phosphate or mixtures thereof, more preferably hydroxyapatite. In this way, a composite coating may be produced on an implant, where the top layer is resorbed in a matter of months and stimulates bone growth, and the TiP or ZrP bottom layer serves as a stable substrate which is not resorbed over time.

The invention includes any and all combinations of preferred features disclosed herein. In particular, all the preferred features of the coated substrates are also preferred features of coated substrates obtainable by the methods of the invention.

EXAMPLES

The following are non-limiting examples of the invention.

Abbreviations

PBS—phosphate buffered saline
Sa—arithmetical mean height of the surface
SBF—simulated body fluid Example 1a. Production of a ZrP Coating Dispersion In beaker 1 the following ingredients were mixed to form a microemulsion:
17.5 g Pluronic L64 (BASF)
53.75 g p-xylene (Sigma-Aldrich)
3.75 g $H_2O$
0.500 g $ZrCl_4$ (Sigma-Aldrich)
In beaker 2 the following ingredients were mixed to form a microemulsion:
17.5 g Pluronic L64 (BASF)
53.75 g p-xylene (Sigma-Aldrich)
3.75 g $H_2O$
0.495 g $H_3PO_4$ 85% (Fluke)
The contents of beaker 2 were poured into beaker 1 and the resulting mixture was placed on a magnetic stirrer for 24 hours. The resulting dispersion was translucent with a slight haze.

Example 1 b. Production of Another ZrP Coating Dispersion

In beaker 1 the following ingredients were mixed to form a microemulsion:
12.5 g Triton X-100 (Sigma-Aldrich)
3.1 g 1-hexanol (Sigma-Aldrich)

23.5 g cyclohexane
3.40 ml $H_2O$
0.626 g $ZrOCl_2*8H_2O$

In beaker 2 the following ingredients were mixed to form a microemulsion:

12.5 g Triton X-100 (Sigma-Aldrich)
3.1 g 1-hexanol (Sigma-Aldrich)
23.5 g cyclohexane
3.40 ml $H_2O$
0.448 g $H_3PO_4$ 85% (Fluke)

The contents of beaker 2 were poured into beaker 1 and the resulting mixture was placed on a magnetic stirrer for 24 hours. The resulting dispersion was semi-translucent and slightly cloudy.

Example 2. Production of a TiP Coating Dispersion

In beaker 1 the following ingredients were mixed to form a solution:

17.5 g Pluronic L64 (BASF)
53.75 g p-xylene (Sigma-Aldrich)
0.500 g titanium isopropoxide (Sigma-Aldrich)

In beaker 2 the following ingredients were mixed to form a microemulsion:

17.55 g Pluronic L64 (BASF)
53.75 g p-xylene (Sigma-Aldrich)
7.5 g $H_2O$
0.406 g $H_3PO_4$ 85% (Fluke)

The contents of beaker 2 were poured into beaker 1 and the resulting mixture was placed on a magnetic stirrer for 24 hours. The resulting dispersion was translucent with a slight haze.

Example 3a. Application of a Nanosized ZrP Coating onto a Titanium Disc

A titanium disc, 6 mm in diameter and 2 mm thick, was roughened with grade 400 sand paper and then cleaned with isopropanol, 1 M $HNO_3$ and water. The disk was placed on a spin coating device, followed by the addition of 85 µl of the coating dispersion prepared in Example 1a. Using the spin coating device, the disc was then rotated at 2200 rpm for 3 seconds. The disc was allowed to dry at room temperature and was subsequently placed in a furnace for 5 minutes, set at 450° C. in an oxygen enriched atmosphere. After the heat treatment, the disk was allowed to cool to room temperature and was analysed by SEM and XPS. A SEM image of the coated disc is shown in FIG. 1a (Scale bar=200 nm). As seen from this high magnification image, the coating has a porous appearance, with pore sizes of 10-30 nm.

Example 3b. Application of a Nanosized ZrP Coating onto a Titanium Disc

Figure 1B:
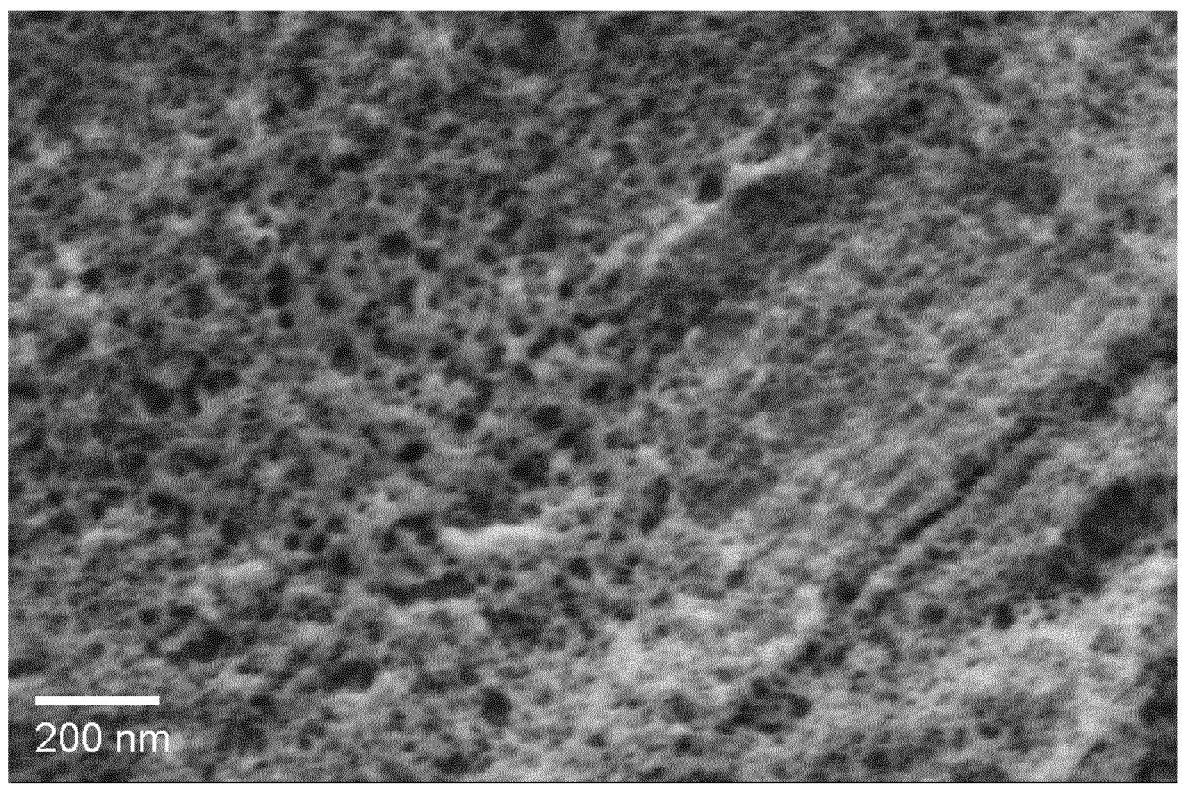
FIG. 1b. SEM image of ZrP coating of the invention on a titanium disc, using a Triton X-100/1-hexanol/cyclohexane/water system. Scale bar=200 nm.

To examine the appearance of a coating dispersion with a different composition, a titanium disc, 6 mm in diameter and 2 mm thick, was roughened with grade 400 sand paper and then cleaned with isopropanol, 1 M $HNO_3$ and water. The disk was placed on a spin coating device, followed by the addition of 85 µl of the coating dispersion prepared in Example 1 b. Using the spin coating device, the disc was then rotated at 2200 rpm for 3 seconds. The disc was allowed to dry at room temperature and was subsequently placed in a furnace for 5 minutes, set at 450° C. in an oxygen enriched atmosphere. After the heat treatment, the disk was allowed to cool to room temperature and was analysed by SEM and XPS. A SEM image of the coated disc is shown in FIG. 1b (Scale bar=200 nm). As seen from this image, the coating has a similar appearance as with the coating dispersion described in Example 1a.

Example 4. Application of a Nanosized TiP Coating onto a Titanium Disc

Figure 2:
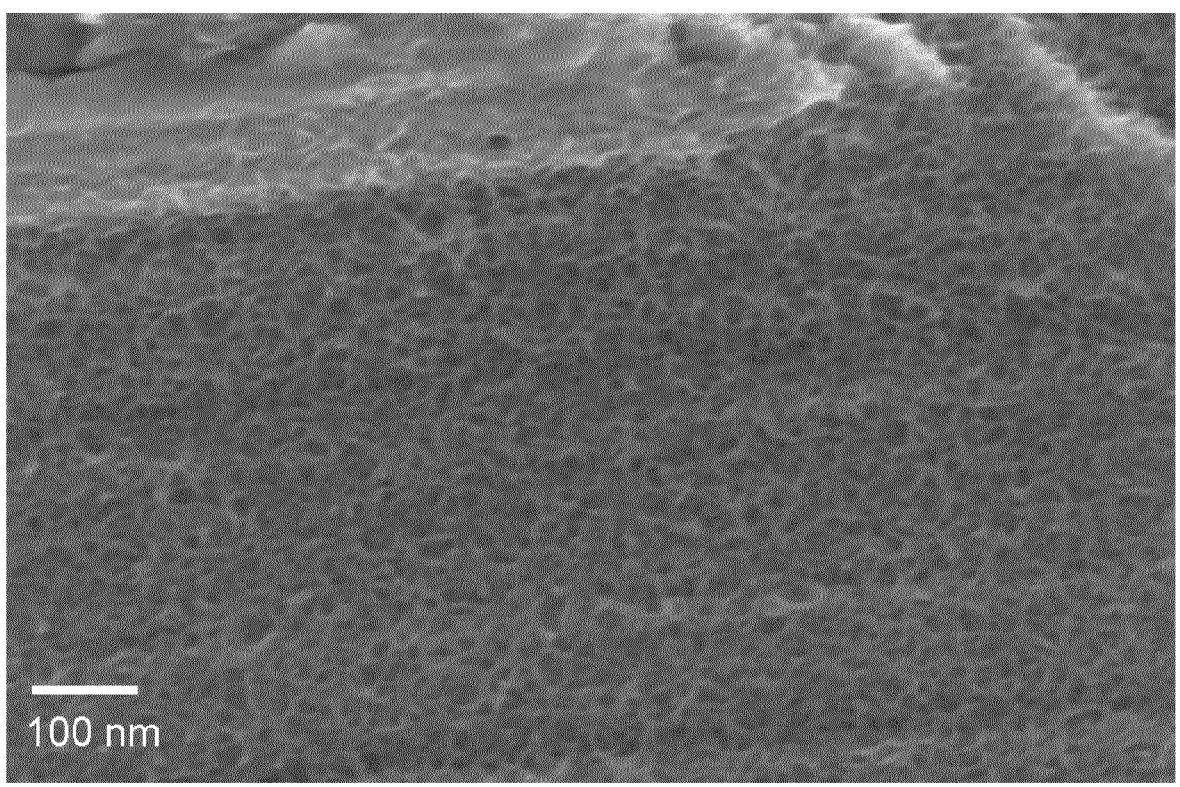
FIG. 2. SEM image of TiP coating of the invention on a titanium disc. Scale bar=100 nm.

A titanium disc, 6 mm in diameter and 2 mm thick, was roughened and cleaned according to Example 3. The disc was placed on a spin coating device followed by addition of 85 µl of the coating dispersion prepared in Example 2. Using the spin coating device, the disk was then rotated at 3000 rpm for 10 seconds. The disc was heat treated according to Example 3a. The disc was allowed to cool to room temperature and was analysed by SEM and XPS. A SEM image of the coated disc is shown in FIG. 2 (Scale bar=100 nm). As seen the coating has a similar appearance to the ZrP coating, with a porous, foam-like structure. The pore sizes are in the same range as for the ZrP coating. Striations from the machining are visible in the upper part of this image, and interestingly these patterns continue on the coated part, which shows that the coating follows the underlying topography.

Example 5. Application of a Nanosized ZrP Coating onto a PEEK Screw

Figure 3:
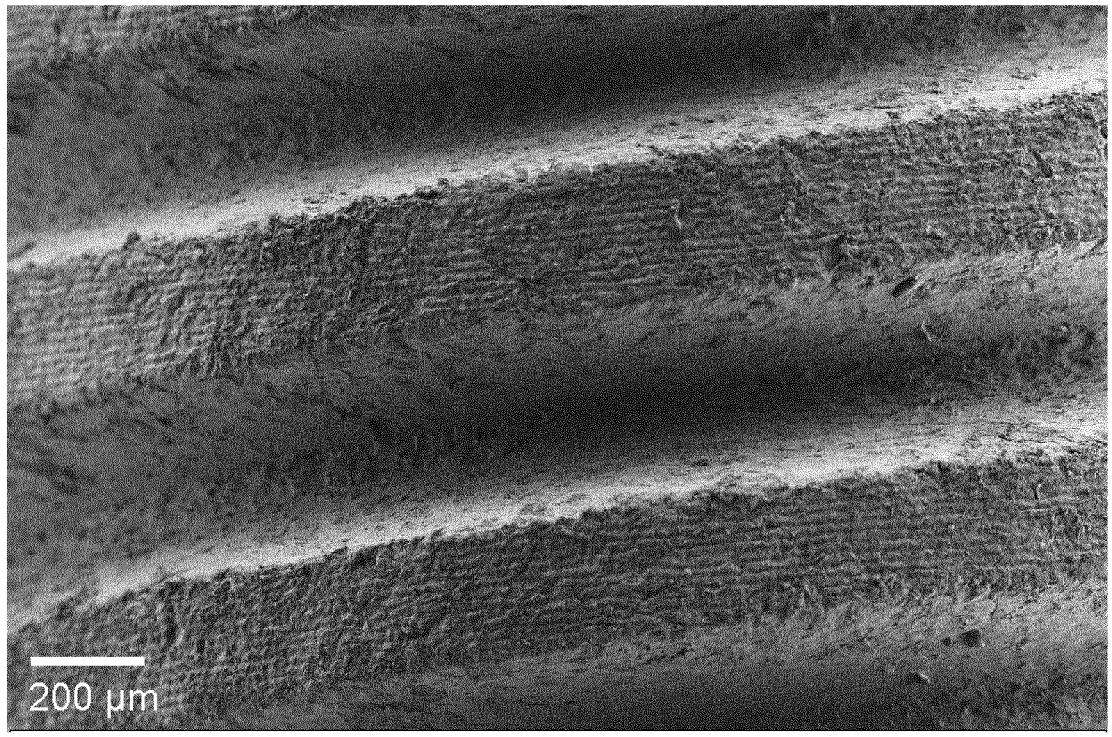
FIG. 3. SEM images at low and high magnifications of a blasted PEEK screw coated with ZrP according to the invention, scale bars=200 μm and 200 nm.
Figure 3:
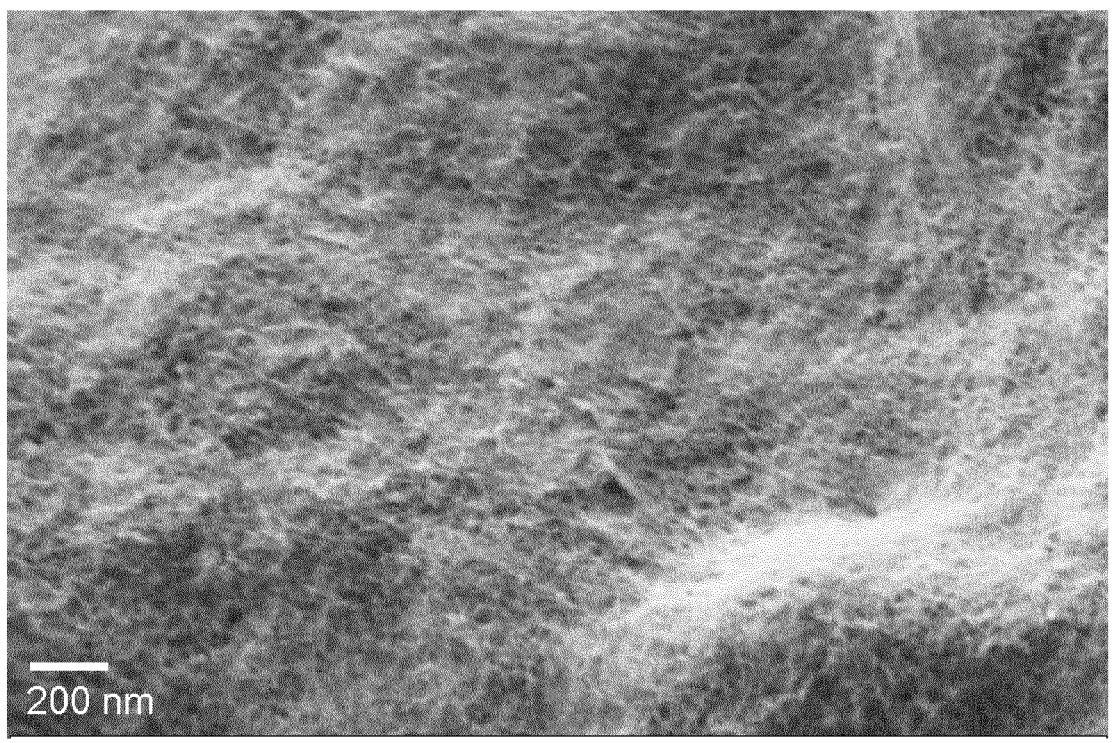

PEEK screws (machined from PEEK-Optima, Invibio Ltd), 3.5 mm in diameter and 4 mm long, were blasted with resorbable blasting media (hydroxyapatite, RBM WAS 180-300, MedicalGroup Corp, France) to a roughness (Sa) of 1.1 µm. The roughness before the blasting was 0.55 µm (Sa). The RBM media was dissolved and the implants were coated by applying 85 µl of the coating dispersion prepared in Example 1a on top of the implants, and allowed to rotate at 2500 rpm and 5 seconds on a spin coating device. The implant screw was allowed to dry at room temperature and was subsequently placed in a furnace for 5 minutes, set to 340° C. in an oxygen enriched atmosphere. After the heat treatment, the screw was allowed to cool to room temperature and was analysed by SEM and XPS. SEM images of the coated screw at low (40×) and high magnification (40 000×) are shown in FIG. 3. At low magnifications (upper image, scale bar 200 µm) the coating is not visible, and it can be seen that it does not change the topography at this size level. At high magnification (lower image, scale bar 200 nm) the coating can be seen as a porous layer on top of the substrate.

Figure 4:
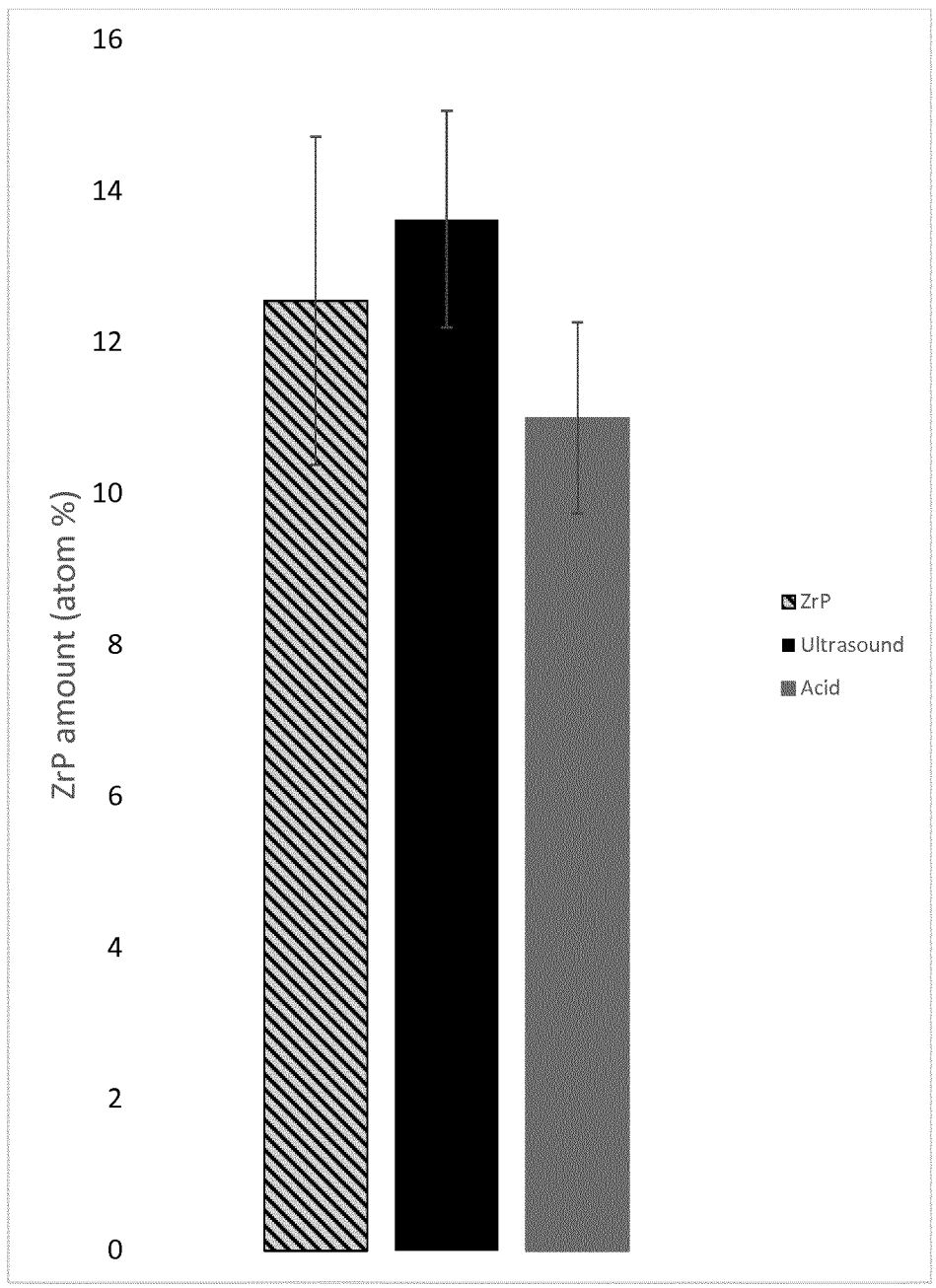
FIG. 4. Total amount of ZrP as measured with XPS (calculated as the sum of atomic % of Zr and P), for ZrP discs immersed in acetic acid or ultrasonicated in water.

Example 6. Investigation of the Adhesion and Acid Tolerance of a ZrP Coating Machined PEEK screws, 3.5 mm and 4 mm in diameter, were coated according to the parameters used in Example 5. One group of screws was immersed in a beaker of 200 ml water and ultrasonicated for 5 minutes. Another group was immersed in a beaker of 200 ml of acetic acid with a pH of 4. The screws were cleaned, dried and analyzed by XPS. The result of this measurement is shown in FIG. 4 (total amount of ZrP as measured with XPS, calculated as the sum of atomic % of Zr and P). As this Figure shows, the ZrP coating was unaffected by ultrasonication or exposure to acidic pH.

Example 7. Investigation of the Mineralization Properties of a ZrP Coating

Figure 5:
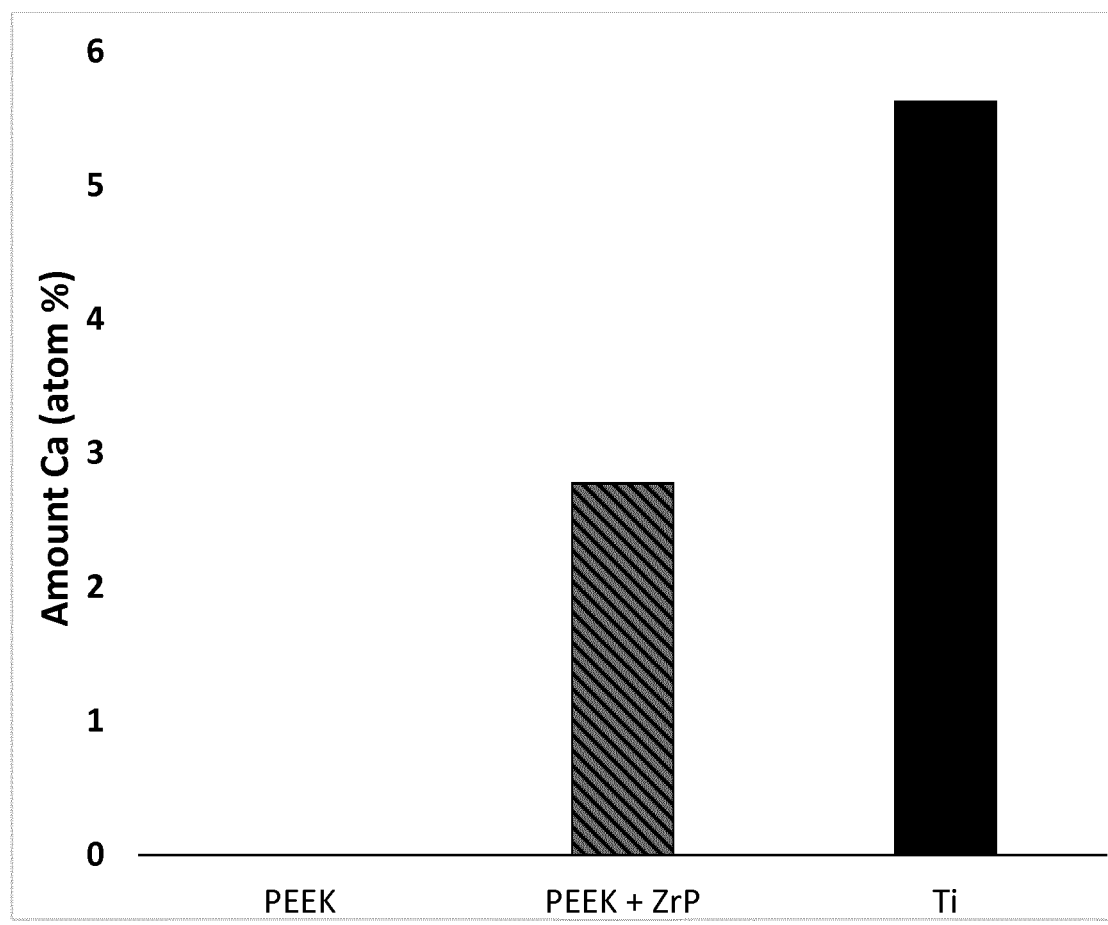
FIG. 5. Calcium content of uncoated and ZrP coated PEEK and titanium discs immersed in Simulated Body Fluid (SBF), as measured with XPS.

Titanium and PEEK discs, 6 mm in diameter and 2 mm thick, were roughened and cleaned as described in Example 3a. Titanium discs were coated using the parameters described in Example 3a. The PEEK discs were coated with spinning at 2500 rpm for 3 seconds, a temperature of 325° C. for 5 minutes and with an oxygen atmosphere. The discs were then immersed in Dulbecco's PBS (1×) with Ca & Mg from PAA Cell Culture Company (a simulated body fluid). After 24 hours, the discs were removed from the SBF bath and rinsed thoroughly with type 1 (ultrapure) water. The discs were allowed to dry and were then analysed by XPS. The calcium amount on the different samples, as measured with XPS, is shown in FIG. 5. As seen from this Figure, no calcium was detected on the untreated PEEK. For the ZrP coated discs, 2.8% calcium was detected. As a comparison, titanium discs were also included in this test, and the calcium amount on these discs was approximately twice the amount detected on the ZrP coated PEEK discs (5.6%). This shows that the ZrP coating on the PEEK substrate produces a surface which induces mineralization, a property which is known to be very important for bone cell growth.

Figure 6:
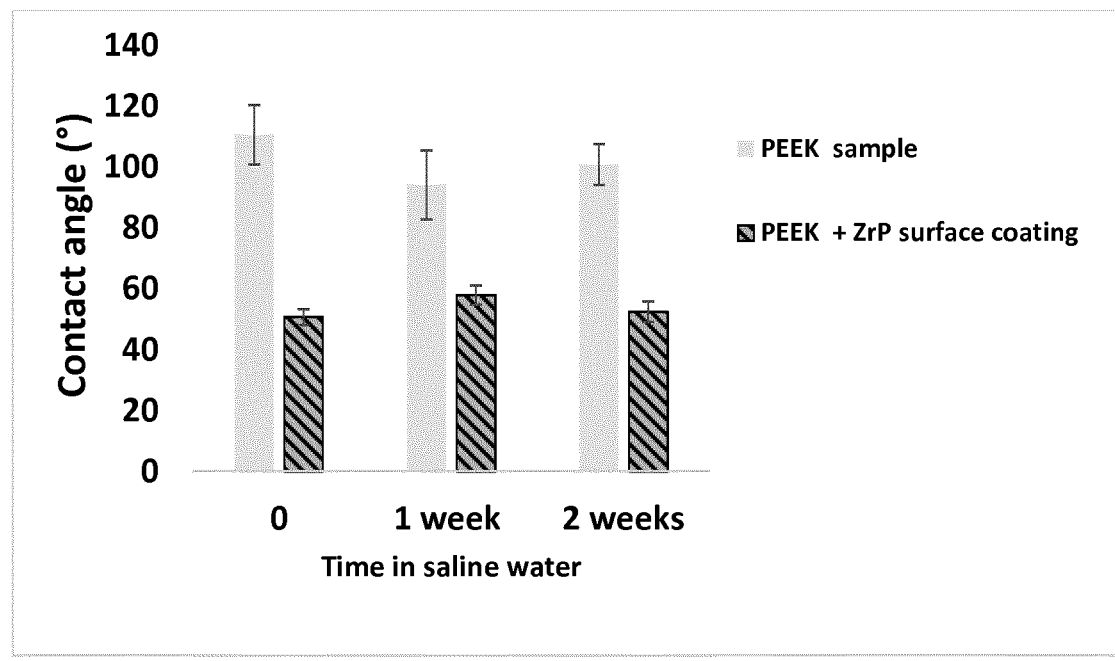
FIG. 6. Contact angle measurements on uncoated and ZrP coated PEEK after 1 and 2 weeks in simulated salt water solution.

Example 8. Investigation of the Coating Stability and Hydrophilicity of a ZrP Coating on PEEK Disks, Placed in Simulated Salt Water PEEK discs, 6 mm in diameter and 2 mm thick, were roughened and cleaned according to Example 3a. Half of the discs were coated with ZrP as described in Example 3a and the other half were left uncoated and used as control samples. The discs were immersed in a saline solution designed to simulate the composition of natural sea water, with 24.615 g/l NaCl, 4.105 g/l $Na_2SO_4$, 11.06 g/l $MgCl_2.6H_2O$ and 1.558 g/l $CaCl_2.2H_2O$. The solution was adjusted to pH 8 with a 0.2 M NaOH solution. Half of the discs were coated with ZrP and the other half were left uncoated and used as control samples. Discs were removed from the saline solution after 1 and 2 weeks. The discs were washed in type 1 water, dried and the water contact angle was analysed. The result of this analysis is shown in FIG. 6. As seen, before the immersion in saline solution the ZrP coated discs were hydrophilic with a contact angle of around 45°, whereas the uncoated discs were hydrophobic with a contact angle of around 110°. The difference in contact angle for the coated and uncoated discs was approximately the same after 1 and 2 weeks; the coated discs stayed hydrophilic with contact angles between 45-50° while the uncoated discs were hydrophobic with contact angles between 90-100°. This demonstrates that the hydrophilicity was preserved for the ZrP coated samples.

Example 9. Preparation of a Combination Coating of ZrP and HA

A PEEK disc, 6 mm in diameter and 2 mm thick, was roughened and cleaned as described in Example 3a. The PEEK disc was placed on a spin coating device, followed by addition of 75 μl of the coating dispersion described in Example 1a. Using the spin coating device, the disc was rotated at 1300 rpm for 3 seconds. The disc was allowed to dry at 120° C. for 10 minutes thereafter allowed to cool at room temperature for 5 minutes. Subsequently the disc was placed in a furnace for 5 minutes, set at 325° C. in an air-fed atmosphere. After the heat treatment, the disc was allowed to cool to room temperature.

Figure 7:
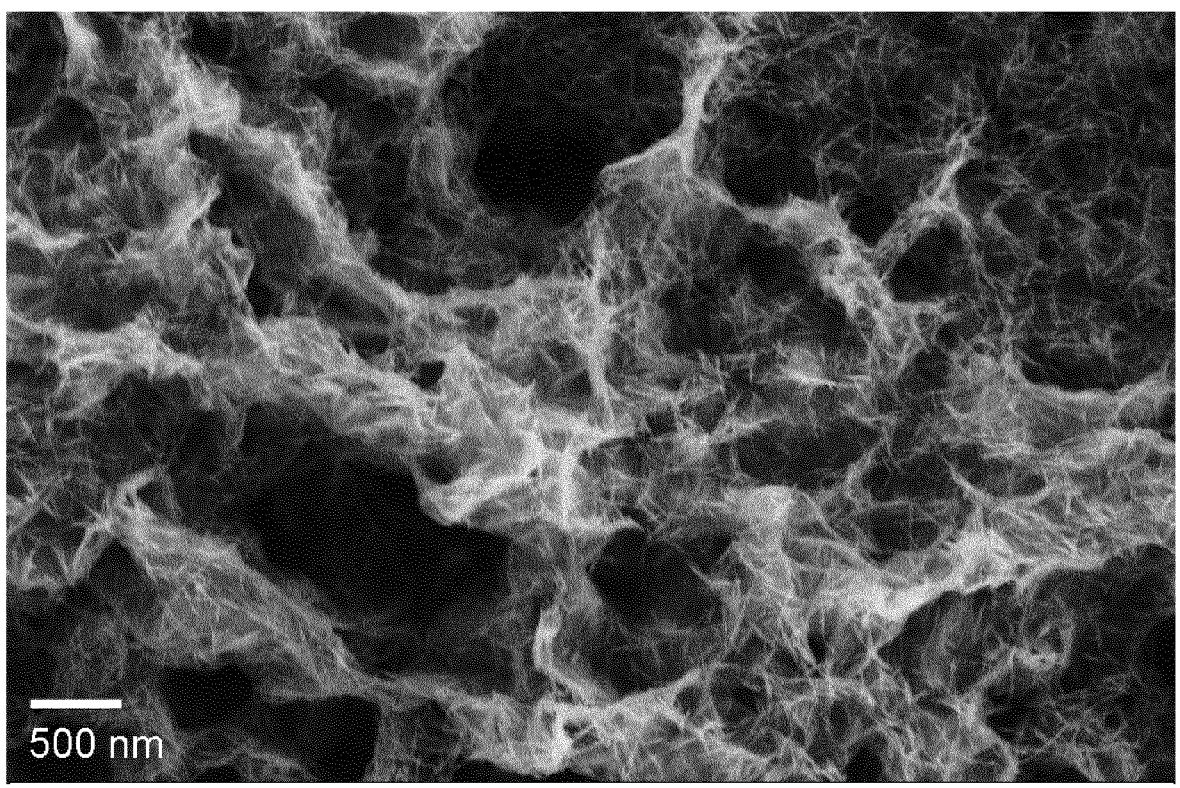
FIG. 7. SEM image of a PEEK disc first coated with ZrP, and then coated with nanosized HA. Scale bar=500 nm.

The coated PEEK was again placed on a spin coating device and the above process was repeated with the exception that the coating dispersion used was the dispersion described in Example 2 of WO2005/123579. After the heat treatment, the disc was allowed to cool to room temperature and was analysed by XPS. This analysis showed 8.8% Ca and 5.5% P with trace levels of Zr, which indicates that the CaP coating behaved in the same way as if formed directly on top of a titanium substrate. A SEM image of the disc is shown in FIG. 7 (scale bar=500 nm). As seen the HA layer follows the underlying structure of the ZrP layer, forming a thin layer of uniform needle-shaped HA crystals on top of the ZrP coating.

Figure 8:
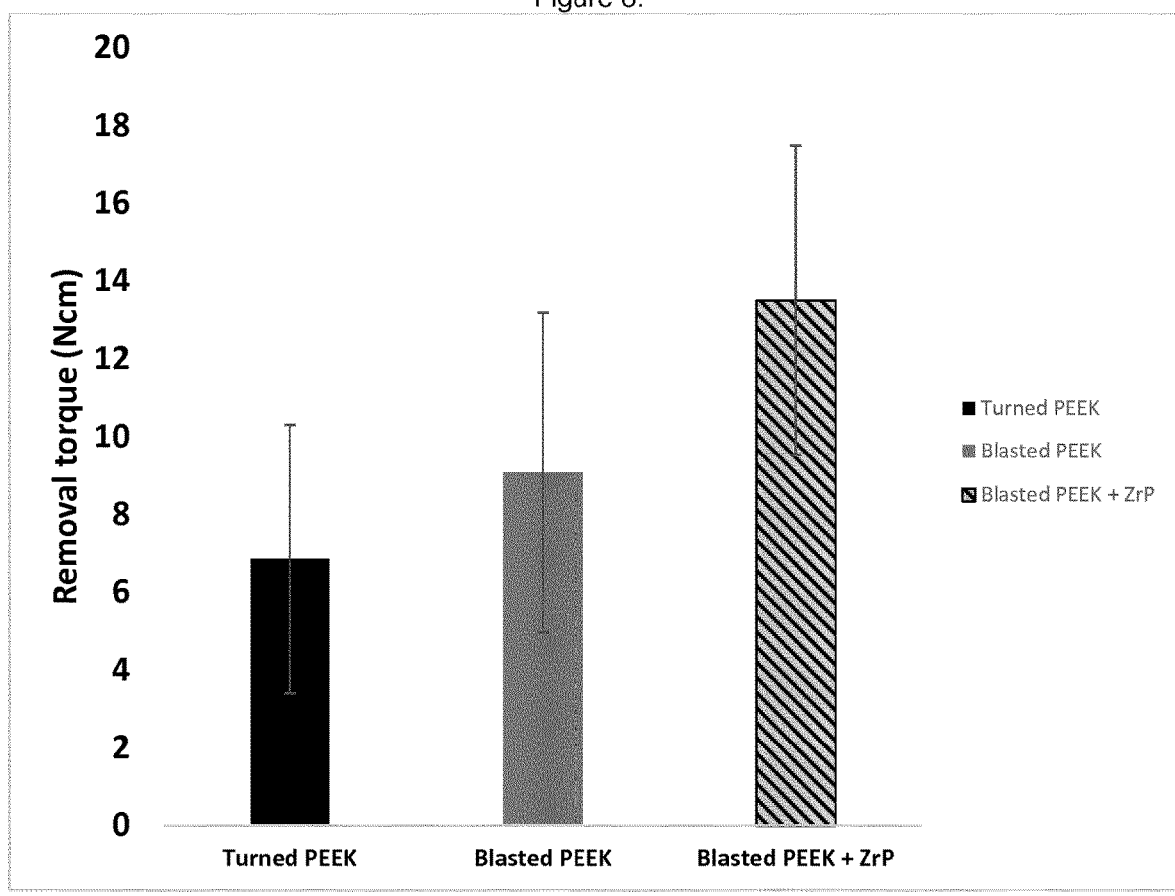
FIG. 8. Removal torque values of blasted PEEK implants, uncoated and ZrP coated, after 6 weeks of implantation in rabbit tibia.

Example 10. In Vivo Study of the Osseointegration Properties of ZrP Coated PEEK Implants PEEK screws were blasted and coated according to Example 5. Machined PEEK implants, blasted PEEK and ZrP coated implants, all of the same screw shape macro geometry, were subsequently implanted in the tibia of 7 rabbits. The implants were allowed to heal for 6 weeks, after which the animals were sacrificed, and the removal torque of the implants was measured with a Tohnichi torque gauge. The removal torque values (in Ncm) for the different groups are shown in FIG. 8. It can be seen that blasting increased the anchoring strength of the implants, from 6.9 Ncm for the turned to 9.1 Ncm for the blasted ones. Coating with ZrP increased the anchoring strength to 13.5 Ncm. Statistical significance (Mann-Whitney U) was p(0.05) for ZrP coated vs. blasted screws. This shows that the ZrP coating transforms the bioinert PEEK surface to a surface which osseointegrates.

Example 11. Investigation of Hydrophilicity During Storage

Figure 9:
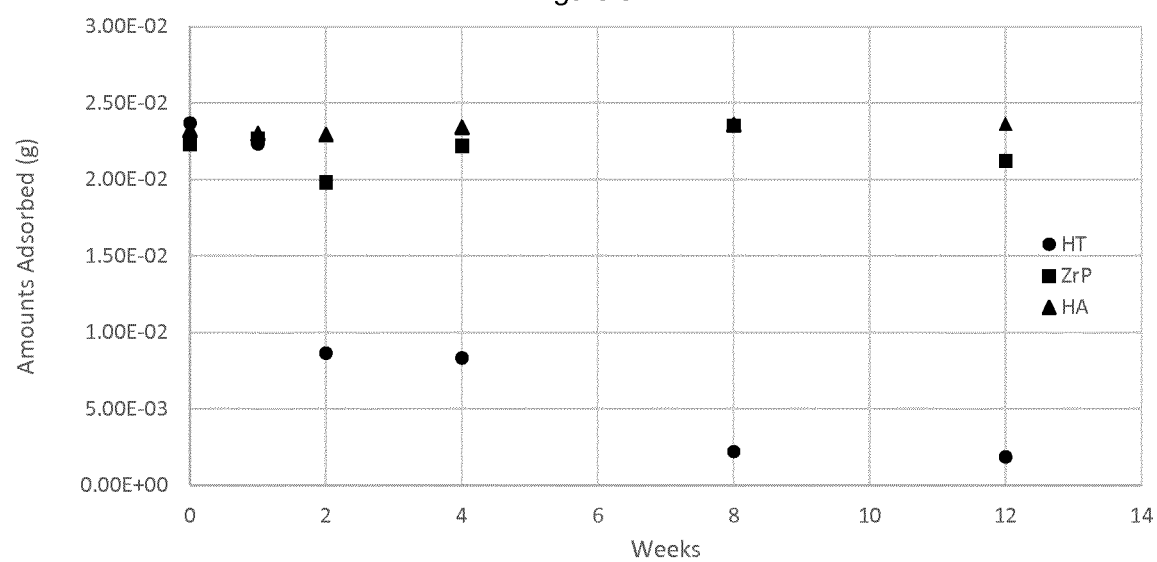
FIG. 9. Liquid adsorption of water on dental implant screws after different storage times. ●=heat treated, ■=ZrP coated, ▲=HA coated.

Acid-etched dental implants with a roughness of approximately 1.0 μm (Sa) were coated with ZrP with the coating dispersion described in Example 1a, using a temperature of 450° C. in an oxygen enriched atmosphere for the heat treatment. In a second test group, the same type of implants was coated with HA according to WO2005/123579. In a third test group, the same type of implants was heat treated using the same temperature as for the ZrP and HA treated implants. All implants were placed in glass vials and were stored for 1, 2, 4, 8 and 12 weeks. After each time period, liquid adsorption was measured. Separate glass vials were used for each implant and for each time, i.e. after the liquid adsorption measurement, the implant was discarded. The liquid adsorption was measured by lowering the implant into a beaker containing type 1 water, until the lower 3 threads were below the water surface. The implants were then allowed to adsorb water for 30 seconds, and the implant was thereafter raised so that no part of the implant touched the water surface. The implant was then placed on an analytical balance and the weight was recorded. By comparing the weight of the implant before and after the liquid immersion, the weight of the adsorbed water could be calculated. The result of these measurements is shown in FIG. 9 (●=heat treated (HT), ■=ZrP coated, ▲=HA coated). As can be seen from FIG. 9, both the ZrP and the HA treated screws retained their hydrophilicity over time. The heat treated screws were initially hydrophilic, but this hydrophilicity decayed during storage.

The invention claimed is:
1. A substrate comprising a first coating on a surface thereof, the first coating comprising amorphous nanosized titanium phosphate particles, amorphous nanosized zirco- nium phosphate particles, or a mixture thereof, wherein the first coating has a thickness of from about 1 to about 1000 nm, wherein the amorphous nanosized titanium phosphate particles and/or the amorphous nanosized zirconium phosphate particles in the first coating have a specific surface area of from about 5 $m^2$/g to about 400 $m^2$/g.

2. The substrate according to claim 1, wherein the substrate is an implant suitable for use in vivo.

3. The substrate according to claim 1, further comprising a second coating comprising calcium phosphate.

4. The substrate according to claim 1, wherein the first coating further comprises an antibiotic.

5. The substrate according to claim 1, wherein the implant is a dental screw, hip stem, spinal fusion cage, ostomy bag port, bone anchored hearing aid, dental implant abutment or an external fixation device.

6. The substrate according to claim 1, wherein the substrate is made from a metal, a ceramic, a graphitic material or a polymer.

7. The substrate according to claim 6, wherein the metal is selected from titanium and its alloys, zirconium and its alloys, stainless steel, tantalum, NiTi alloys and cobalt-chrome alloys; the ceramic is selected from alumina, zirconia, alumina toughened zirconia, and $Si_3N_4$; the graphitic material is selected from graphene and pyrocarbon; and the polymer is selected from polypropylene, polyethylene, polysulfone, polyether ketone ketone, poly(styrene), poly(carbonate), poly(ethylene terephthalate) and polyether ether ketone.

8. A method of forming the substrate of claim 1, the method comprising:
 a) mixing a solution comprising a zirconium precursor and/or a titanium precursor in an organic solvent with a water-in-oil emulsion comprising a phosphate precursor, and allowing the zirconium precursor and/or the titanium precursor and the phosphate precursor to react together to form a dispersion comprising the amorphous nanosized zirconium phosphate and/or the amorphous nanosized titanium phosphate particles;
 b) applying said dispersion to the surface of the substrate;
 c) optionally creating an even layer of the dispersion on the substrate; and
 d) removing water and/or the organic solvent from the dispersion to form the first coating on the substrate.

9. The method according to claim 8, wherein the water-in-oil emulsion further comprises one or more surfactants.

10. The method according to claim 8, further comprising forming a second coating comprising calcium phosphate on the substrate.

11. The method according to claim 10, wherein the second coating is formed on top of the first coating.

12. A substrate comprising a porous coating on a surface thereof, the porous coating comprising:
 a fusion of amorphous nanosized titanium phosphate particles, amorphous nanosized zirconium phosphate particles, or a mixture thereof, wherein the porous coating has a thickness of about 1 nm to 99 nm,
 wherein the amorphous nanosized titanium phosphate particles and/or the amorphous nanosized zirconium phosphate particles in the porous coating have a specific surface area of from about 5 $m^2$/g to about 400 $m^2$/g.

13. The substrate according to claim 12, wherein the porous coating has a thickness of from about 5 nm to about 80 nm.

14. The substrate according to claim 12, wherein the substrate is made from a metal, a ceramic, a graphitic material, a polymer or silicon.

15. The method according to claim 8, wherein the solution comprises the zirconium precursor and the method comprises allowing the zirconium precursor and the phosphate precursor to react together to form a dispersion comprising the amorphous nanosized zirconium phosphate particles.

16. The method according to claim 8, wherein the solution comprises the titanium precursor and the method comprises allowing the titanium precursor and the phosphate precursor to react together to form a dispersion comprising the amorphous nanosized titanium phosphate particles.

17. The method according to claim 8, wherein the solution comprises the zirconium precursor and the titanium precursor and the method comprises allowing the zirconium precursor and the phosphate precursor to react together and allowing the titanium precursor and the phosphate precursor to react together to form a dispersion comprising the amorphous nanosized zirconium phosphate particles and the amorphous nanosized titanium phosphate particles.

18. The substrate of claim 1, wherein the first coating further comprises titanium phosphate and/or zirconium phosphate agglomerates.

19. The substrate of claim 18, wherein the titanium phosphate and/or zirconium phosphate agglomerates are fused amorphous nanosized titanium phosphate particles and/or amorphous nanosized zirconium phosphate particles.

20. The substrate of claim 1, wherein the first coating is a continuous, porous coating.

21. The substrate of claim 18, wherein the first coating is a continuous, porous coating.

22. The substrate of claim 1, wherein the first coating is hydrophilic.

23. The substrate of claim 1, wherein the substrate is a sensor.

24. The substrate of claim 1, wherein the substrate is a medical device.

25. The substrate of claim 1, wherein the first coating has a thickness from about 1 to about 500 nm.

26. The substrate of claim 1, wherein the first coating has a thickness from about 1 to about 99 nm.

27. The substrate of claim 20, wherein the first coating has a thickness from about 1 to about 300 nm.

* * * * *

UNITED STATES PATENT AND TRADEMARK OFFICE
CERTIFICATE OF CORRECTION

PATENT NO. : 12,268,795 B2
APPLICATION NO. : 16/967047
DATED : April 8, 2025
INVENTOR(S) : Kjellin et al.

It is certified that error appears in the above-identified patent and that said Letters Patent is hereby corrected as shown below:

In the Specification

Column 14, Line 56: correct "(Fluke)" to read --(Fluka)--

Column 15, Line 10: correct "(Fluke)" to read --(Fluka)--

Column 15, Line 29: correct "(Fluke)" to read --(Fluka)--

Column 17, Lines 31-32: correct "24.615 g/I NaCl, 4.105 g/I Na$_2$SO$_4$, 11.06 g/I MgCl$_2$.6H$_2$O and 1.558 g/I CaCl$_2$.2H$_2$O" to read --24.615 g/l NaCl, 4.105 g/l Na$_2$SO$_4$, 11.06 g/l MgCl$_2$·6H$_2$O and 1.558 g/l CaCl$_2$·2H$_2$O--

Signed and Sealed this
Twelfth Day of August, 2025

Coke Morgan Stewart
*Acting Director of the United States Patent and Trademark Office*